US010893851B2

(12) United States Patent
Kruecker

(10) Patent No.: US 10,893,851 B2
(45) Date of Patent: Jan. 19, 2021

(54) SYSTEM AND METHOD FOR MOTION COMPENSATION IN MEDICAL PROCEDURES

(71) Applicant: KONINKLIJKE PHILIPS N.V., Eindhoven (NL)

(72) Inventor: Jochen Kruecker, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 50 days.

(21) Appl. No.: 15/567,648

(22) PCT Filed: May 9, 2016

(86) PCT No.: PCT/IB2016/052623
§ 371 (c)(1),
(2) Date: Oct. 19, 2017

(87) PCT Pub. No.: WO2016/178198
PCT Pub. Date: Nov. 10, 2016

(65) Prior Publication Data
US 2018/0146955 A1 May 31, 2018

Related U.S. Application Data

(60) Provisional application No. 62/158,011, filed on May 7, 2015.

(51) Int. Cl.
*A61B 8/08* (2006.01)
*A61B 8/00* (2006.01)
*G06T 7/30* (2017.01)

(52) U.S. Cl.
CPC .......... *A61B 8/5276* (2013.01); *A61B 8/4245* (2013.01); *A61B 8/483* (2013.01); *A61B 8/5246* (2013.01); *G06T 7/30* (2017.01); *A61B 8/5261* (2013.01); *G06T 2207/10132* (2013.01); *G06T 2207/20092* (2013.01)

(58) Field of Classification Search
CPC ........................................... G06T 2207/20092
See application file for complete search history.

(56) References Cited

U.S. PATENT DOCUMENTS

| | | | |
|---|---|---|---|
| 6,856,310 B2 * | 2/2005 | Ditt | G06F 3/0346 345/156 |
| 9,001,226 B1 * | 4/2015 | Ng | H04N 5/23203 348/211.11 |
| 9,626,589 B1 * | 4/2017 | Graham | G06T 3/4038 |
| 10,357,092 B2 * | 7/2019 | Kustra | A45D 24/36 |

(Continued)

*Primary Examiner* — Gandhi Thirugnanam
(74) *Attorney, Agent, or Firm* — Sherry Austin

(57) ABSTRACT

A system for fusing images to account for motion compensation includes an imaging modality configured to obtain a baseline image and current images. A live tracking system is configured to track an imaging instrument for capturing the baseline image and the current images, the live tracking system having a coordinate system registered with the baseline image and the current images. A pose analyzer unit is configured to employ field of view differences between a pose for the baseline image and a pose for a current view image using the live tracking system to generate success parameters. The success parameters are conveyed to the user to provide feedback on image acquisition for motion compensation between the baseline image and the current view image.

21 Claims, 4 Drawing Sheets

(56) References Cited

U.S. PATENT DOCUMENTS

| | | | |
|---|---|---|---|
| 2003/0026469 A1* | 2/2003 | Kreang-Arekul | G06K 9/32 382/132 |
| 2006/0093192 A1* | 5/2006 | Bechtel | G06K 9/00013 382/126 |
| 2009/0161826 A1* | 6/2009 | Gertner | A61N 5/1017 378/65 |
| 2009/0161827 A1* | 6/2009 | Gertner | A61F 9/008 378/65 |
| 2009/0298017 A1* | 12/2009 | Boerjes | A61B 5/4547 433/214 |
| 2010/0190629 A1* | 7/2010 | Eijkelkamp | B65H 45/18 493/445 |
| 2010/0256495 A1* | 10/2010 | Kruecker | A61B 8/481 600/458 |
| 2010/0268085 A1* | 10/2010 | Kruecker | A61B 8/0833 600/443 |
| 2010/0310140 A1* | 12/2010 | Schneider | G06K 9/6247 382/130 |
| 2011/0190629 A1 | 8/2011 | Guenther et al. | |
| 2012/0022348 A1* | 1/2012 | Droitcour | A61B 5/0507 600/323 |
| 2012/0293511 A1* | 11/2012 | Mertelmeier | A61B 6/025 345/419 |
| 2012/0293667 A1* | 11/2012 | Baba | H04N 13/246 348/246 |
| 2013/0058555 A1* | 3/2013 | Miao | G06K 9/00214 382/132 |
| 2013/0060146 A1* | 3/2013 | Yang | A61B 5/055 600/476 |
| 2013/0266178 A1* | 10/2013 | Jain | G06T 7/70 382/103 |
| 2014/0105474 A1* | 4/2014 | Lee | G06T 7/0012 382/128 |
| 2014/0193053 A1* | 7/2014 | Kadoury | G06T 11/008 382/131 |
| 2014/0194793 A1* | 7/2014 | Nakata | A61B 5/0816 601/48 |
| 2014/0200440 A1* | 7/2014 | Iannotti | A61B 5/061 600/424 |
| 2014/0213906 A1* | 7/2014 | Li | A61B 8/5207 600/459 |
| 2016/0005229 A1* | 1/2016 | Lee | G06F 3/0488 345/419 |
| 2016/0014396 A1* | 1/2016 | Glinec | A61C 9/0053 433/29 |
| 2016/0106381 A1* | 4/2016 | Aase | A61B 5/7455 600/461 |
| 2017/0105701 A1* | 4/2017 | Pelissier | A61B 8/4254 |
| 2017/0262982 A1* | 9/2017 | Pagoulatos | G06T 7/0012 |
| 2018/0085002 A1* | 3/2018 | Glinec | G06T 7/73 |
| 2018/0146955 A1* | 5/2018 | Kruecker | G06T 7/30 |
| 2018/0225993 A1* | 8/2018 | Buras | A61B 8/085 |

* cited by examiner

SYSTEM AND METHOD FOR MOTION COMPENSATION IN MEDICAL PROCEDURES

CROSS-REFERENCE TO PRIOR APPLICATIONS

This application is the U.S. National Phase application under 35 U.S.C. § 371 of International Application Serial No. PCT/IB2016/052623, filed on May 9, 2016, which claims the benefit of U.S. Application Ser. No. 62/158,011, filed on May 7, 2015. These applications are hereby incorporated by reference herein.

BACKGROUND

Technical Field

This disclosure relates to motion compensation and more particularly to systems, interfaces and methods for accounting for patient motion in medical images.

Description of the Related Art

Multi-modality "fusion" imaging of ultrasound with a prior image (of the same or other imaging modality) can be enabled using electromagnetic (EM) tracking of an ultrasound probe and registration of the EM coordinate system with the coordinate system of the prior image. Automatic methods to establish the registration may be based on acquisition of an EM-tracked three-dimensional (3D) ultrasound (US) volume (called a baseline 3DUS), followed by manual or automatic image-based registration of the baseline 3DUS to the prior static image (e.g., a computed tomography (CT) image).

If internal organ motion occurs, e.g., due to respiration, the registration between the live ultrasound imaging and the prior image will no longer be accurate. In particular, if the operator is planning an intervention such as a needle insertion into a tumor, the operator will typically request a breath hold to interrupt the tumor motion. However, the position of the tumor during this breath hold typically differs from the position during baseline 3DUS acquisition. Thus, the fusion image with the prior static image may suffer from inaccuracies.

Image-based registration methods to re-register a current or "live" ultrasound image back to the baseline 3DUS have been attempted to compensate for organ motion. However, such registration methods are not robust or accurate if the overlap or similarity between the images to be registered is insufficient.

SUMMARY

In accordance with the present principles, a system for fusing images to account for motion compensation includes an imaging modality configured to obtain a baseline image and current images. A live tracking system is configured to track an imaging instrument for capturing the baseline image and the current images, the live tracking system having a coordinate system registered with the baseline image and the current images. A pose analyzer unit is configured to employ field of view differences between a pose for the baseline image and a pose for a current view image using the live tracking system to generate success parameters. The success parameters are conveyed to provide feedback on optimal image acquisition for motion compensation between the baseline image and the current view image.

Another system for fusing images to account for motion compensation includes an ultrasound system configured to obtain a baseline ultrasound image and live ultrasound images. A live tracking system is configured to track an ultrasound probe for the baseline image and the current images, the live tracking system having a coordinate system registered with the baseline image and the current images. A pose analyzer unit is configured to employ field of view differences between a pose for the baseline image and a pose for a current view image using the live tracking system to generate success parameters. The success parameters are conveyed to provide feedback on optimal image acquisition for motion compensation between the baseline image and the current view image. A pose guidance unit is configured to provide direction to a user to achieve a satisfactory pose for the current view image. A registration system is configured to register static images with one or more of the baseline images and the current images.

A method for fusing images to account for motion compensation includes capturing a baseline image; obtaining live images of a target area; tracking an imaging instrument to obtain a pose for capturing the baseline image and to obtain a pose for a current view of the live images such that a tracking system has its coordinate system registered with the baseline image and the live images; analyzing a pose for a current view to compare field of view differences between the pose for the baseline image and the pose for the current view using the tracking system to generate success parameters; conveying the success parameters to provide feedback on optimal image acquisition for motion compensation between the baseline image and the current view; and if the success parameters are adequate, acquiring a new image at the pose of the current view.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
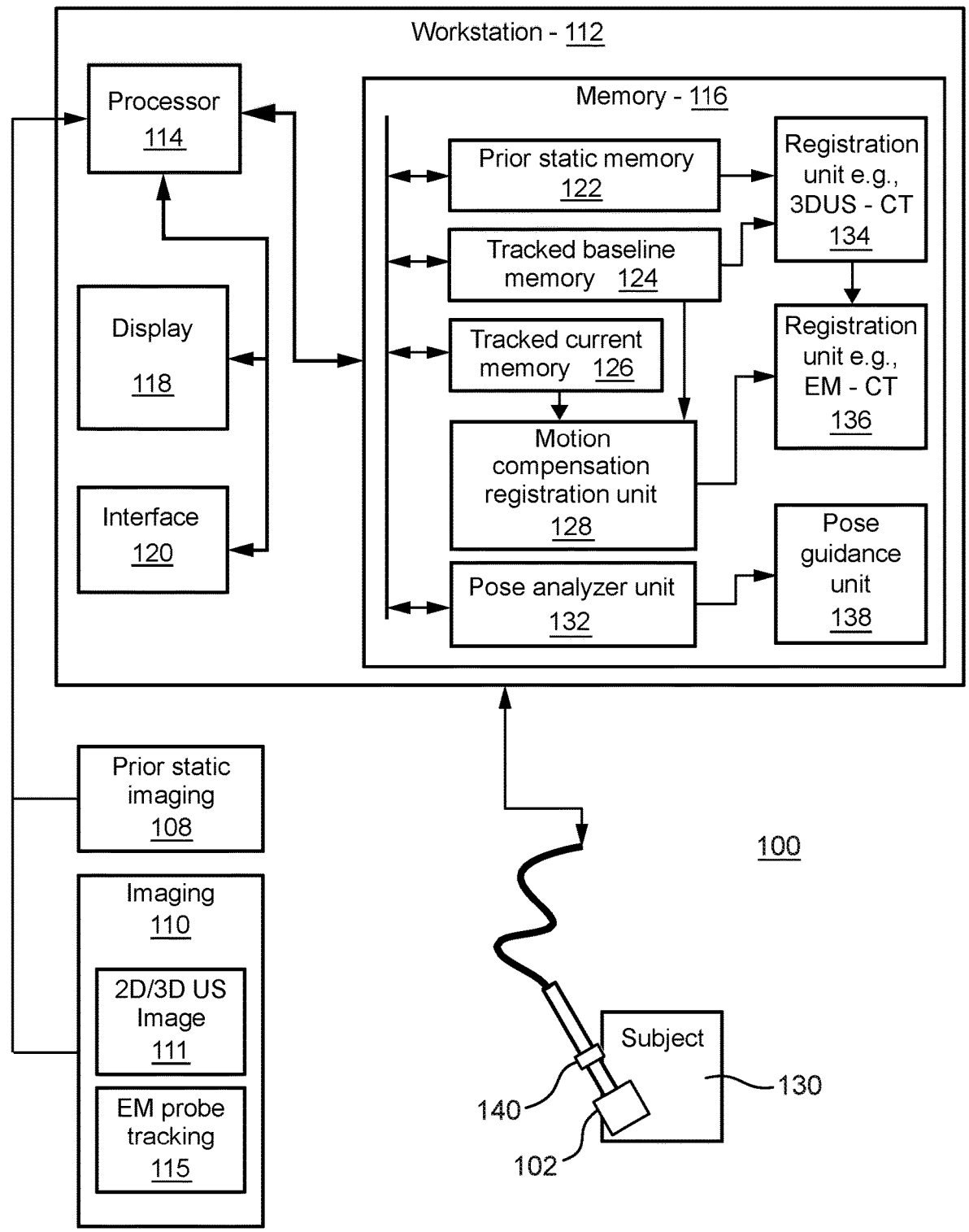
FIG. 1 is a block/flow diagram showing an image fusion system which compensates for motion in accordance with one embodiment.

In accordance with the present principles, systems, methods and interfaces provide feedback to an operator about success parameters of a current view, and may provide guidance for a user to achieve a view with optimal success parameters. Success parameters are parameters related to overlap or similarity between images (fields of view (FOV))

to be registered. Without motion compensation, fusion imaging becomes less accurate and less useful when organ motion occurs. Manual motion compensation is cumbersome, inaccurate, and user-dependent. Automatic image-based motion compensation is fast and accurate only if a live image to be used for registration has sufficient overlap and similarity ("success parameters") with the baseline image. Since it is not trivial for the operator to assess the success parameters of an ultrasound view, the operator may acquire 3DUS (three-dimensional ultrasound) images and attempt motion compensation by "trial and error", resulting in failed registration attempts, wasted time, and operator dissatisfaction.

The present principles provide feedback about the success parameters of the current view, before the image is acquired and motion compensation is attempted, and provide guidance to a view that has high or optimal success parameters. The present principles result in efficient motion compensation in multi-modality "fusion" imaging procedures. Motion is compensated using image-based registration of a "live" or "current" ultrasound volume relative to a prior "static" ultrasound volume. The static volume, in turn, may be pre-registered to another modality such as a computed tomography (CT) image. The registration-based motion compensation uses the live and static images to find sufficient similarity and overlap (success parameters).

In one embodiment, fields of view are compared to identify similar poses for imaging equipment to enable sufficient overlap (success parameters) between baseline and live images. An interface provides live feedback on such success parameters to guide the user to an acquisition of the live image that permits successful and accurate registration with the static image.

In one motion compensation embodiment, the operator acquires a live, electromagnetic (EM)-tracked 3D ultrasound (3DUS) image that can be registered with a prior static 3DUS. Based on the EM tracking and the known field-of-view (FOV) of the 3DUS, the relative pose and overlap between the current view and the static image can be computed. This information is provided to the operator to identify a view that is suited for motion compensation while also imaging a desired target area (e.g., a tumor). In an alternative embodiment, the operator inputs the desired target area, and the system computes one or several suitable views to image the target area with sufficient overlap and pose similarity to the static image to permit successful motion compensation. The system may then provide guidance to the operator to place an ultrasound probe in or near a pre-computed pose for 3DUS acquisition. In other embodiments, image similarity between baseline and current views may be employed to find an optimal field of view match.

It should be understood that the present invention will be described in terms of medical imaging instruments; however, the teachings of the present invention are much broader and are applicable to any imaging instruments where motion compensation is useful. In some embodiments, the present principles are employed in tracking or analyzing complex biological or mechanical systems. In particular, the present principles are applicable to internal tracking procedures of biological systems and in procedures in all areas of the body, such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element, such as, e.g., an image, image region or overlay, is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for image fusion is illustratively shown in accordance with one embodiment. System 100 may include a computer or other workstation or console 112 from which a procedure is supervised and/or managed and/or imaging fusion is performed. Workstation 112 preferably includes one or more processors 114 and memory 116 for storing programs and applications. Memory 116 may store a plurality of modules, units, applications and/or programs configured to fuse images from same or different imaging modalities. It should be understood that the modules being described as stored in memory 116 may in fact include electronic circuits or other hardware components including connectors, wires, circuit boards, integrated circuit chips, memory devices, etc. in addition to or instead of software.

Memory 116 includes a pose analyzer unit 132, which receives spatial pose tracking information from a baseline 3DUS stored in tracked baseline memory 124 and from live/current image 111, which may be stored in tracked current memory 126 when acquired at a current/live position of an imaging probe 102, to compute success parameters. The imaging probe 102 may include an ultrasound probe for live or real-time imaging of a subject 130. The imaging probe 102 is tracked using electromagnetic (EM) tracking 115, although other tracking technologies may be employed. Pose analyzer unit 132 passes the information (success parameters) to a display 118, and optionally to a pose guidance unit 138. The pose guidance unit 138 may receive user input (target area) via a graphical user interface on display 118 and/or interface 120. While the pose analyzer unit 132 computes overlap and similarity (success parameters) for measuring field of view similarity, the pose guidance unit 138 provides direct information on how to reposition the probe 102 to obtain optimal fields of view for images. As an example, the pose analyzer unit 132 may provide an overlap percentage (e.g., 55% overlap) as feedback, while the pose guidance unit 138 could provide instructions, e.g., "move probe to the left", to achieve a higher overlap percentage.

The user is provided with real time feedback and/or guidance to achieve a best pose for performing a task, replicating the baseline image, increasing the probability of a good registration with prior static images, etc.

Display 118 may also permit a user to interact with the workstation 112 and its components and functions, or any other element within the system 100. This is further facilitated by the interface 120 which may include a keyboard, mouse, a joystick, a haptic device, microphone, speakers, lights or any other peripheral or control to permit user feedback from and interaction with the workstation 112. The interface 120 may provide feedback and guidance that is displayed to the operator and is thus visible on the system's display 118, audible if audio feedback is employed, vibrational if haptic feedback is employed, etc.

System 100 provides an ultrasound fusion imaging system based on spatial tracking (e.g., EM tracking using and EM tracking device 140 and EM probe tracking 115) of the ultrasound probe 102. It should be understood that other tracking technologies may also be employed, e.g., optical shape sensing, etc. A registration unit 134, e.g., a multi-modality registration module, provides registration for different modalities with or to a prior static image stored in memory 122. The prior static image 122 may be captured by any imaging modality 108, such as, e.g., CT, magnetic resonance, X-ray, US, etc. The imaging modality 108 may be present during a procedure or the static images 122 may be supplied from a previous procedure or captured image. Registration unit 134 registers the prior static image from memory 122 with an acquired spatially tracked baseline 3DUS volume stored in memory 124.

The information from live probe tracking 115 and a known field-of-view of the ultrasound images 111 from a live imaging modality 110 are employed to continuously compute and display overlap and pose similarity (e.g., relative rotations, etc. that provide success parameters) of a current view with the baseline 3DUS stored in memory 124 before a new image 3DUS 126 is acquired, stored and/or used for registration.

The success parameters may also measure image similarity (e.g., image contrast, brightness, information content or other features) extracted from live images. Note that the image-based success parameters (from live-images) need the acquisition and processing of 2D or preliminary images (111) (e.g., live and/or baseline images), whereas the other success parameters only need the pose tracking information (and knowledge of the ultrasound field of view—but no images needed).

While US is described, other imaging modalities may be employed for imaging modality 110. Note that the image registration is less likely to succeed the smaller the overlap and the larger the relative rotation between the images. A motion compensation unit 128 accounts for motion between the new image 3DUS 126 and the baseline 3DUS image 124 and provides the motion compensation information to a registration unit 136, which is employed to register an EM coordinate system of EM tracker 140 with the static image 122 and provide registration for the baseline image 124 registered to the static images 122 from the registration unit 134.

The motion compensation registration unit 128 computes the differences in images between the baseline images 124 and the tracked current image 126. This information is employed by the pose analyzer unit 132 to compute the success parameters for a current pose before acquiring a new image. It should be understood that while registration units and modules are described individually, registration of the various coordinate systems, computation of transforms and other registration functions may be performed by a single or multiple registration units, engines or programs.

In an alternative embodiment, the system 100 also computes and provides guidance to acquire an optimal view using the post guidance unit 138. A computation of the optimal view may use operator input of a desired target area for imaging, such as a tumor, to find a view that images the tumor while maintaining sufficient success parameters for motion compensation.

The system 100 is operable on a tracking-based ultrasound fusion imaging system, such as the Philips® PercuNav® product, although the present principles may be applied to other devices and may include other imaging modalities. In particularly useful embodiments, the present principles are operable on a system that acquires 3DUS baseline images 124, which, in turn, are registered by the registration unit 134 to the prior static image (e.g., CT) 122 that the live ultrasound image 126 is to be fused with. One goal is to provide an efficient workflow and method for compensation of organ motion that may have occurred since the time the 3DUS baseline image 124 was captured. During fusion imaging, the ultrasound system is typically in "live 2D" mode, and the live 2D images 111 from the ultrasound scanner are fused (via the current registration units 134, 136) with the prior static image (CT) 122.

The operator is interested in fusion-imaging of a particular target area, such as a tumor, and will move the ultrasound probe 102 to explore different ways of visualizing the tumor. Different views of the tumor are possible, but only some may have sufficient overlap and pose similarity (success parameters) with the baseline 3DUS 124 for motion compensation.

The system 100 continuously computes and displays the success parameters, enabling the operator to identify a view of the tumor with sufficient success parameters. The operator optionally proceeds to obtain a breath hold from the patient, acquires a live 2D/3DUS image 111 of the tumor, which is stored in the current view memory 126 once acquired. The motion compensation unit 128 is triggered with the acquisition of the new 3DUS image (stored in memory 126).

The system 100 carries out the motion compensation by registering the live 3DUS image 126 with the baseline 3DUS 124, and using the registration result from registration unit 134 to update the displayed fusion image. The updated fusion image can now be used by the operator to visualize the tumor or to carry out an intervention (such as a needle insertion).

Figure 2:
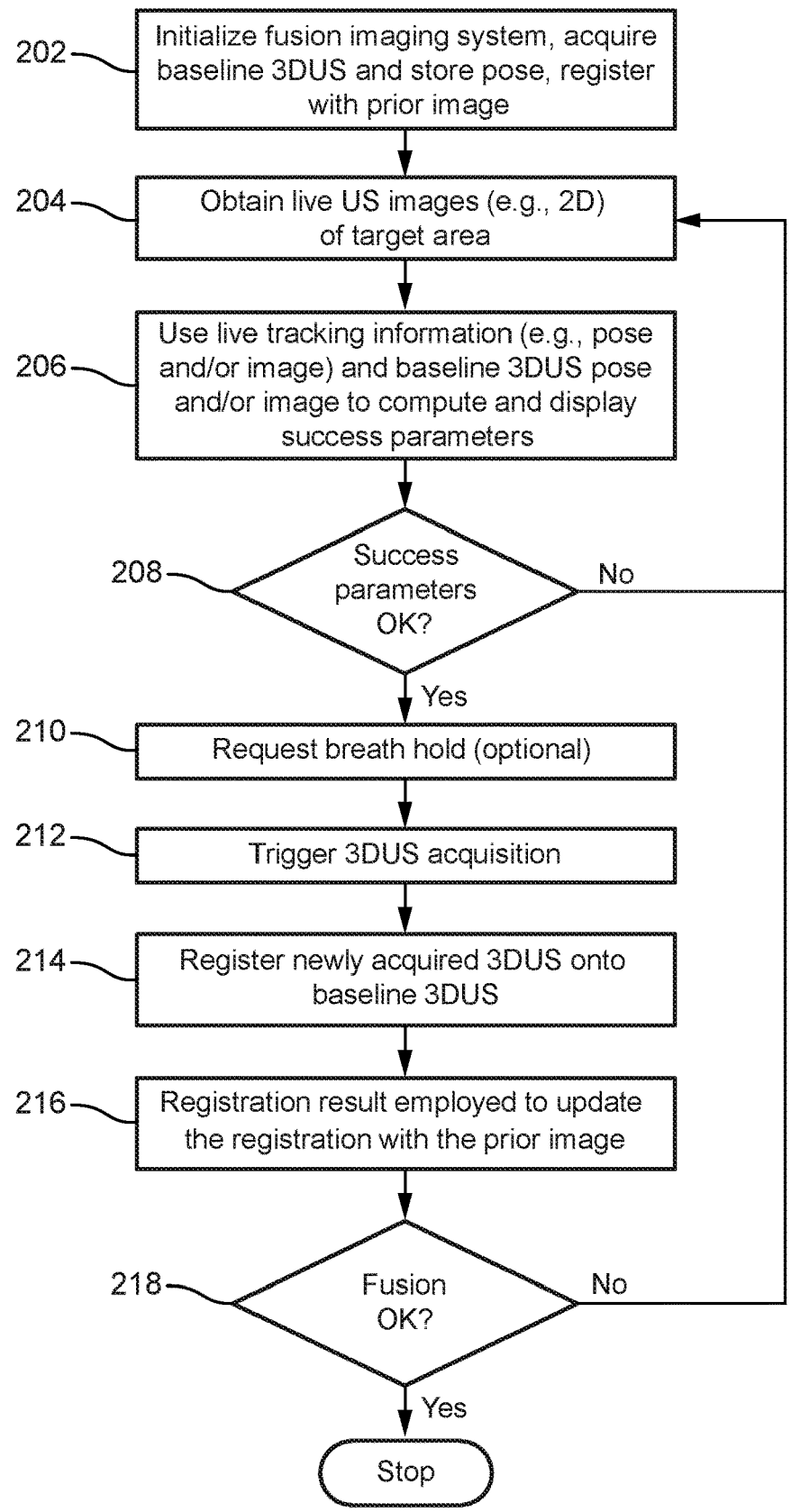
FIG. 2 is a flow diagram showing a method for fusing images while compensating for motion in accordance with an illustrative embodiment.

Referring to FIG. 2, a method for tracking-based ultrasound fusion imaging is illustratively shown. In block 202, the fusion imaging system is initialized. A baseline image is acquired and its pose is stored. The acquired image is registered with a prior image (e.g., a static image of the same volume). In particular, acquisition of a 3DUS baseline image is obtained, which in turn is registered to the prior static image (e.g., CT) that the live ultrasound is to be fused with. In block 204, a live image of a target area is obtained. The live image may be, e.g., a 2D or 3DUS image. The ultrasound system is usually in "live 2D" mode, and the live 2D images from the ultrasound scanner are fused (via the current registration) with the prior static image (CT).

In block 206, live tracking information (e.g., EM pose and/or image features) and the baseline pose and/or image are employed to compute and display success parameters. Optionally, the live 2D image from block 204 may also be used in the calculation of success parameters. Features of the live 2D images such as, e.g., image brightness, contrast, etc. may be employed to detect good imaging conditions for successful motion compensation. One aim is to provide an efficient workflow and method for compensation of organ motion that may have occurred since the time of the 3DUS baseline image. The system continuously computes and displays the success parameters, enabling the operator to identify a view of the tumor with sufficient success parameters.

In block 208, a determination of the quality of the success parameters is performed. If the success parameters are sufficient, the path continues with block 210. Otherwise, the path returns to block 204. An operator is usually interested in fusion-imaging a particular target area, such as a tumor, and will move the ultrasound probe to explore different ways of visualizing the tumor. Different views of the tumor are possible, but only some may have sufficient overlap and pose similarity (success parameters) with the baseline 3DUS for motion compensation.

In block 210, an optional breath hold may be requested of the patient. In block 212, an acquisition of a new image (e.g., 3DUS) is triggered. This occurs when the success parameters are adequate. In block 214, the newly acquired image (e.g., 3DUS) is registered onto the baseline image. The operator may proceed to obtain the breath hold from the patient, acquire a live 3DUS of the tumor in the current view, and trigger the motion compensation with the acquired 3DUS.

In block 216, the registration result from block 214 is employed to update the registration with the prior US image (baseline or previously acquired US image). The system carries out the motion compensation by registering the live 3DUS with the baseline 3DUS, and using the registration result to update the fusion image. In block 218, a determination of the quality of the fusion is made. If the quality is good, then the path ends, and the updated fusion image can now be used by the operator to visualize the tumor or to carry out an intervention (such as a needle insertion). Otherwise, the path returns to block 204 to reattempt to update the fusion image.

Figure 3:
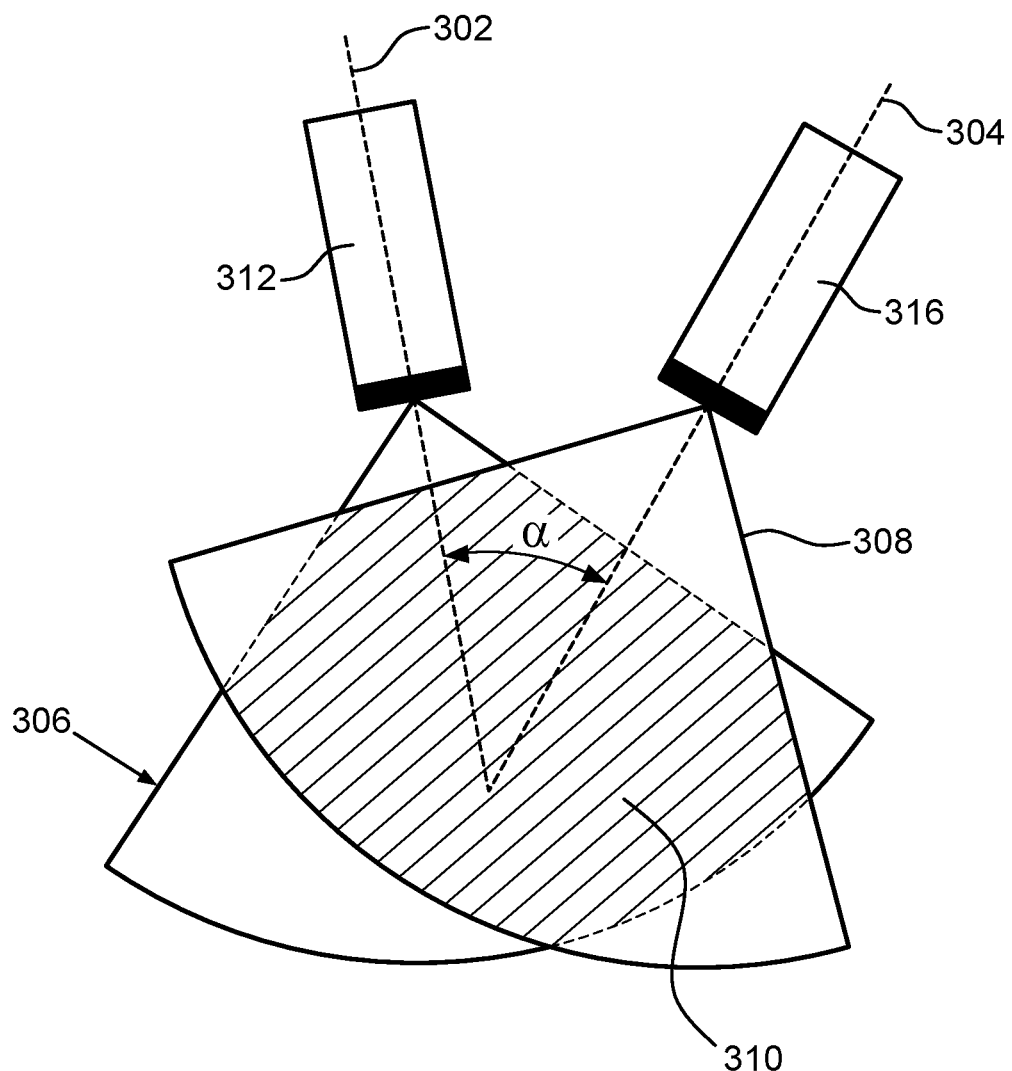
FIG. 3 is a diagram showing fields of view for a baseline and a current pose to determine success parameters in accordance with an illustrative embodiment.

Referring to FIG. 3, a diagram shows ultrasound imaging overlap to describe the computation of success parameters in the pose analyzer unit 132 of FIG. 1. Image overlap and relative pose can be computed as success parameters (shown in FIG. 3 in 2D for simplicity). Ultrasonic probes 312, 314 are each positioned to provide different views 302 and 304, respectively. Using a pose of the baseline 3DUS (transform: $T_{US2EM\_base}$ (US to EM registration for a baseline image)) (view 302) and of a current 3DUS view (transform: $T_{US2EM\_current}$ (US to EM registration for a current image)) (view 304), a relative pose transform $T_{current2base}$ (current image to baseline image fusion)=$\text{inv}(T_{US2EM\_base})$. $T_{US2EM\_current}$ between two views 302 and 304 is computed. In this example, view 302 includes a baseline 3DUS pose and view 304 includes a current 3DUS pose. Known ultrasound fields of view (FOV) (sector images 306 and/or 308) are employed to compute overlap of a hatched image area 310. An image angle difference, a, is computed directly from the relative pose transform $T_{current2base}$. The success parameters may include the angle ($\alpha$) and the hatched area 310. If the angle $\alpha$=0 and the hatched area 310 coincides with the views 302, 304, then there is no motion to be compensated for. Success parameters may also include parameters, such as, e.g., brightness, contrast or other image features, extracted from the 2D US images acquired in the different views.

Referring again to FIG. 1 with continued reference to FIG. 3, the system 100 may provide feedback and guidance for optimizing the success parameters of the ultrasound view. To this end, the pose analyzer unit 132 will be connected to the pose guidance unit 138 to compute the ultrasound probe motion needed to increase or optimize the parameters. This information is passed onto the display 118 to show the instructions to the operator (e.g., "move left", "rotate clockwise"). The pose guidance unit 138 may use the prior static image 122 (e.g., CT) and information derived from it (e.g., skin surface) to determine ultrasound poses that are acceptable (e.g., ultrasound probe touching skin).

In another embodiment, the system 100 may provide feedback and guidance to optimize the success parameters of an ultrasound view that images the user-provided target area. To this end, the interface 120 will permit the operator to enter a target area in the 3DUS baseline 124 or prior static image 122. The information is passed on to the pose guidance unit 138 to compute guidance toward a view that images that target area while maximizing the success parameters.

The pose optimization problem can be computationally solved by the pose analyzer unit 132 by considering the probe positions and rotations as input parameters (possibly constrained to positions on the patient's skin, as derived from the prior static image 122) that are to be optimized, and defining a cost function, f, that is to be minimized, which is inversely related to the likelihood of motion compensation succeeding for a 3DUS acquired at the current pose. One suitable cost function includes:

$$f\_A(p_i)=100/\text{PercentOverlap}(p_i)+w*(1-|\alpha(p_i)|/90) \qquad \text{EQ. 1}$$

where $p_i$ is the set of probe translation and rotation parameters {tx, ty, tz, rx, ry, rz} defining the current pose of the probe;

$f\_A(p_i)$ is the total "cost" associated with pose $p_i$;

PercentOverlap$_{(A)}$ is the relative overlap of the area imaged by the baseline 3DUS and the current 3DUS (e.g., 100× absolute overlap divided by total field of view);

$\alpha(p_i)$ is the rotation angle between the baseline 3DUS and the current 3DUS, in degrees; and w is a weighting factor to balance the relative contributions of the overlap and the rotation metric.

For the embodiment using the user-provided target area, the cost function can be modified to reflect the requirement to image the target area at the same time. For example, $$f\_B(p_i)=f\_A(p_i)/T(p_i) \qquad \text{EQ. 2}$$

where $T(p_i)$ is a unit step function that is 1 if the target area is fully in the current field of view, and very small (e.g., 1e-10) otherwise, such that the "cost" becomes prohibitively large in $f\_B(p_i)$.

Using the cost function or functions, the user may move the US probe and be given audio, visual, haptic, etc. feedback on the display 118 or from the interface 120 as the target area is approached to guide the operator to an optimal pose for motion compensation. The cost function may be configured to evaluate overlap and/or rotation between different image fields of view as well as image parameters in determining image similarity, e.g., from 2D/preliminary and/or baseline images. The pose guidance unit 138 may also employ the cost function or functions for optimal pose and image similarities to provide guidance commands to the user.

Figure 4:
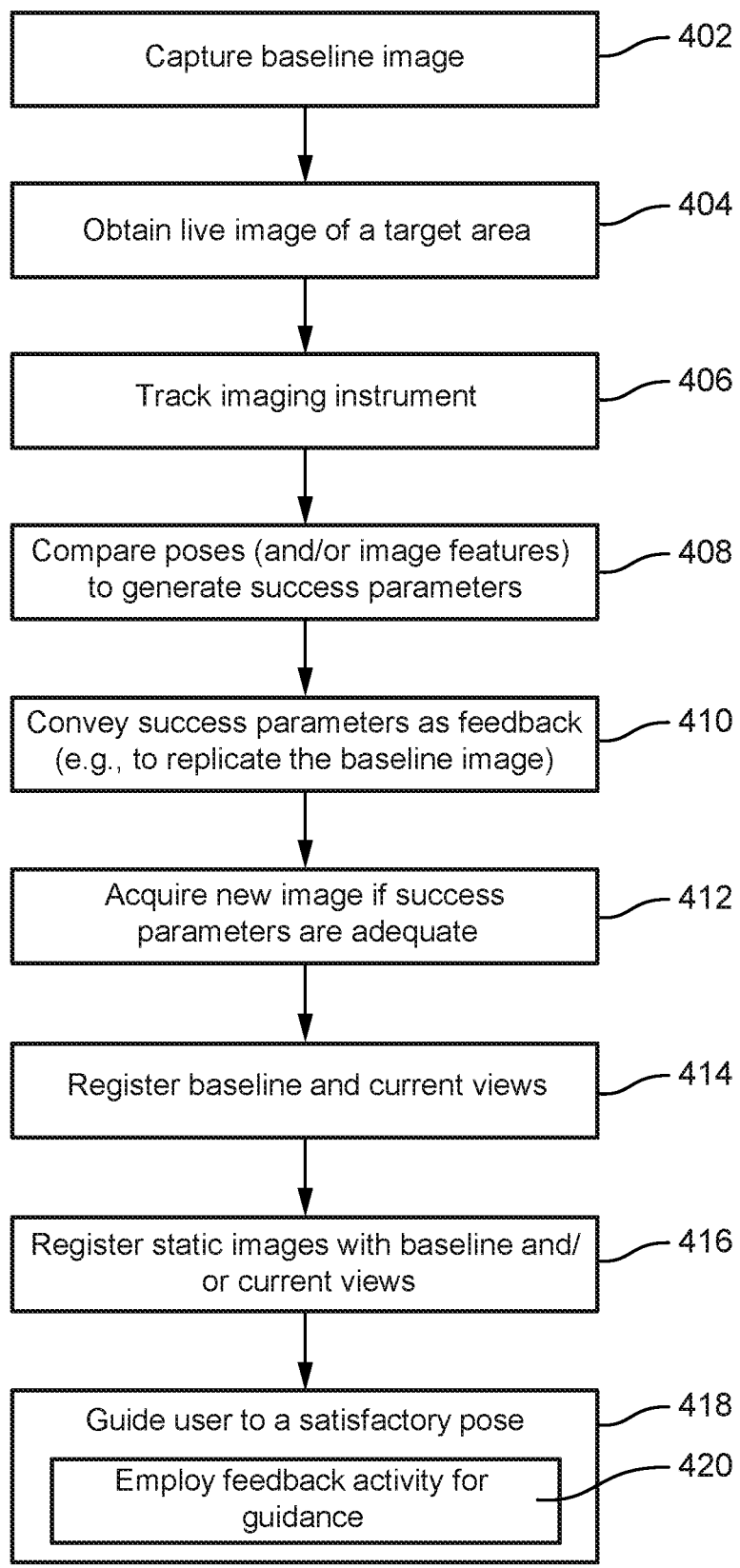
FIG. 4 is a flow diagram showing a method for fusing images while compensating for motion in accordance with another illustrative embodiment.

Referring to FIG. 4, a method for fusing images to account for motion compensation is illustratively shown in accordance with the present principles. In block 402, a baseline image is captured. In block 404, live images of a target area are obtained. The live images may be 2D images or provide a preliminary image. In block 406, an imaging instrument is tracked to obtain a pose for capturing the baseline image and to obtain a pose for a current view of the live images such that a tracking system has its coordinate system registered with the baseline image and the live images. In block 408, a pose for a current view is analyzed to compare field of view differences between the pose for the baseline image and the pose for the current view using the tracking system to generate success parameters. In addition, parameters/image features from the live image and baseline image may be computed and compared as well. In block 410, the success parameters are conveyed to provide feedback on optimal image acquisition for motion compensation between the baseline image and the current view. The success parameters measure field of view overlap and pose similarity between the baseline images and the current view image. The success parameters may include different parameters for achieving overlap, pose similarity and image similarity, e.g., angles, positions, areas, percentages, image contrast, brightness or other quantities or features.

In block 412, if the success parameters are adequate, a new image at the pose of the current view is acquired. This may be a full blown 3D image as opposed to a 2D image or preliminary image. The adequacy of the success parameters may be determined by a user or may be set automatically or as a default. It is determined whether a pose provides a field of view for a current pose comparable to that of the pose of the baseline image to permit a user to replicate the baseline image field of view. For example, a threshold, say, e.g., 90% overlap, between a baseline field of view and a current field of view may be set to determine adequacy. Other criteria are also contemplated.

In block 414, the baseline images and the current view image may be registered. In block 416, static images (e.g., CT, MRI, etc.) may be registered with one or more of the baseline images and the current image(s). This registration may occur at any time and preferably occurs during an early stage (e.g., planning) with regards to the baseline image being registered to the static image.

In block 418, direction is provided to a user to achieve a satisfactory pose for the current view image using a pose guidance unit. The pose guidance unit may include and compute a cost function to evaluate overlap between different image fields of view. The cost function may also consider image parameters between, e.g., a live image (e.g., a preliminary 2D image) and the baseline image. The image parameters may include contrast, brightness, content information, etc.

In block 420, user actions are guided through feedback activity to achieve a satisfactory pose for the current view image. The feedback activity may include at least one of a visual signal (e.g., flash, images), text commands, audio signals (e.g., beeping, voice commands), haptic signals (e.g., vibration intensity, vibration changes), etc.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for system and method for motion compensation in medical procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for fusing images to account for patient motion compensation, comprising:
   an imaging modality configured to obtain a baseline image volume and current image volumes;
   a live tracking circuit configured to track an imaging instrument for capturing the baseline image volume and the current image volumes, the live tracking circuit utilizing a coordinate system registered with the baseline image volume and the current image volumes; and
   a processor configured to provide for patient motion compensation between the baseline image volume and a current image volume based on field of view differences between a pose for the baseline image volume and a pose for the current image volume by generating and conveying to a user success parameters as feedback that indicates to the user a direction to reposition the imaging instrument during image acquisition to account for patient motion by improving overlap and image similarity between the pose for the baseline image volume and the pose for the current image volume after patient motion using the live tracking circuit,
   wherein the processor is further configured to minimize a cost function, wherein the cost function is defined as:

$$f\_A(\rho_i)=100/\text{PercentOverlap}(\rho_i)+w^*(1-|\alpha(\rho_i)|/90),$$

wherein $\rho_i$ is a set of probe translation and rotation parameters $\{tx, ty, tz, rx, ry, rz\}$ defining the pose for the current image volume, $f\_A(\rho_i)$ is a total cost associated with pose $\rho_i$, PercentOverlap($\rho_i$) is a relative overlap of an area imaged by the baseline image volume and the current image volume, $\alpha(\rho_i)$ is a rotation angle between the baseline image volume and the current image volume, in degrees, and w is a weighting factor to balance relative contributions of the overlap and the rotation metric.

2. The system as recited in claim 1, wherein the processor is further configured to generate the success parameters using a measure of at least one of contrast and brightness similarity between the baseline image volume and a live image volume taken at the pose for the current image volume.

3. The system as recited in claim 1, wherein the processor is further configured to register static images with one or more of the baseline image volume and the current image volumes.

4. The system as recited in claim 1, wherein the processor is further configured to determine whether a pose provides a field of view for a current pose that is similar to that of a pose of the baseline image volume to indicate to the user the direction to reposition the imaging instrument to replicate a field of view for the baseline image volume.

5. The system as recited in claim 1, wherein the processor is further configured to produce a user interface that provides direction information to the user indicating the direction to move the imaging instrument to achieve a desired pose for the current image volume.

6. The system as recited in claim 1, wherein the processor is further configured to modify the cost function to evaluate overlap and/or rotation between different image fields of view and/or image parameters between the baseline image volume and the current image volume as $f\_B(\rho_i)=f\_A(\rho_i)/T(\rho_i)$,
   wherein $T(\rho_i)$ is a unit step function that is 1 if a target area is fully in a current field of view, and is reduced otherwise.

7. The system as recited in claim 1, wherein the processor is further configured to produce an interface to guide user actions through feedback activity to achieve a desired pose for the current image volume, the processor being further configured to indicate to the user a direction for an orientation change to reposition the imaging instrument for the current image volume.

8. The system as recited in claim 7, wherein the feedback activity includes at least one of a visual signal, a text command, an audio signal and a haptic signal to guide the user actions to the desired pose.

9. The system, as recited in claim 1, wherein the processor is further configured:
   to provide direction to a user where to reposition and orient the imaging instrument to achieve a desired pose for the current image volume; and
   to register static images with one or more of the baseline image volume and the current image volumes.

10. The system as recited in claim 9, wherein the success parameters measure overlap, pose similarity and/or image similarity between the baseline image volume and the current image volume.

11. The system as recited in claim 9, wherein the processor is further configured to register the baseline image volume and the current image volumes.

12. The system as recited in claim 9, wherein the processor is further configured to determine whether a pose provides a field of view for a current pose that is similar to that of a pose of the baseline image volume to permit a user to replicate a field of view of the baseline image volume.

13. The system as recited in claim 9, wherein the cost function evaluates overlap and/or rotation between different image fields of view and/or image parameters between the baseline image volume and the current image volume.

14. The system as recited in claim 9, wherein the processor is further configured to produce an interface to guide user actions through feedback activity to achieve a pose for the current image volume, wherein the feedback activity includes at least one of a visual signal, a text command, an audio signal and a haptic signal to direct the user actions to the direction to move the imaging instrument to the desired pose.

15. A method for fusing images to account for patient motion compensation, comprising:
   capturing a baseline image volume;
   obtaining live images of a target volume;
   tracking an imaging instrument to obtain a pose for capturing the baseline image volume and to obtain a pose for a current image volume of the live images such that a tracking system has its coordinate system registered with the baseline image volume and the live images;
   providing for patient motion compensation between the baseline image volume and a current image volume based on field of view differences between a pose for the baseline image volume and a pose for the current image volume including minimizing a cost function which inversely relates to a likelihood of motion compensation succeeding for a 3D image acquired at the current image volume to generate and convey to a user success parameters feedback that indicates to the user a direction to reposition the imaging instrument during image acquisition to account for patient motion by improving overlap and image similarity between the pose for the baseline image volume and the pose for the current image volume after patient motion using the tracking system;

wherein the cost function is defined as:

$$f\_A(\rho_i)=100/\text{PercentOverlap}(\rho_i)+w*(1-|\alpha(\rho_i)|/90),$$

wherein $\rho_i$ is a set of probe translation and rotation parameters $\{tx, ty, tz, rx, ry, rz\}$ defining the pose for the current image volume, $f\_A(\rho_i)$ is a total cost associated with pose $\rho_i$, PercentOverlap$(\rho_i)$ is a relative overlap of an area imaged by the baseline image volume and the current image volume, $\alpha(\rho_i)$ is a rotation angle between the baseline image volume and the current image volume, in degrees, and w is a weighting factor to balance relative contributions of the overlap and the rotation metric; and determining when the success parameters satisfy a threshold criteria, and if so, acquiring a new image at the pose of the current view.

16. The method as recited in claim 15, wherein generating the success parameters comprises measuring at least one of contrast and brightness similarity between the baseline image volume and a live image volume taken at the pose of the current image volume.

17. The method as recited in claim 15, further comprising registering the baseline image volume and the current image volume.

18. The method as recited in claim 15, further comprising determining whether a pose provides a field of view for a current pose that is similar to that of the pose of the baseline image volume to permit a user to replicate a field of view for the baseline image volume.

19. The method as recited in claim 15, further comprising providing through a user interface direction to the user indicating the direction to move the imaging instrument to achieve a pose for the current image volume using a pose guidance unit.

20. The method as recited in claim 15, comprising modifying the cost function to evaluate overlap between different image fields of view and/or image parameters between baseline image volume and live image volumes as $f\_B(\rho_i) = f\_A(\rho_i)/T(\rho_i)$, wherein $T(\rho_i)$ is a unit step function that is 1 if a target area is fully in a current field of view, and is reduced otherwise.

21. The method as recited in claim 15, further comprising providing a user interface directing user actions through feedback activity to achieve a pose for the current image volume, wherein the feedback activity includes at least one of visual signals, text commands, audio signals and haptic signals directing the user actions to the desired pose by indicating to the user a direction for an orientation change to reposition the imaging instrument for the current image volume.

* * * * *